(12) United States Patent
Lasenby et al.

(10) Patent No.: US 10,092,221 B2
(45) Date of Patent: Oct. 9, 2018

(54) ANALYSIS OF BREATHING DATA

(71) Applicant: PNEUMACARE LIMITED, Cambridge (GB)

(72) Inventors: Joan Lasenby, Cambridge (GB); Willem Hessel De Boer, Cambridge (GB)

(73) Assignee: PNEUMACARE LIMITED (GB)

( * ) Notice: Subject to any disclaimer, the term of this patent is extended or adjusted under 35 U.S.C. 154(b) by 232 days.

(21) Appl. No.: 14/647,490

(22) PCT Filed: Nov. 27, 2013

(86) PCT No.: PCT/GB2013/053140
§ 371 (c)(1),
(2) Date: May 27, 2015

(87) PCT Pub. No.: WO2014/083337
PCT Pub. Date: Jun. 5, 2014

(65) Prior Publication Data
US 2015/0305657 A1    Oct. 29, 2015

(30) Foreign Application Priority Data

Nov. 27, 2012  (GB) .................................. 1221336.9
Sep. 4, 2013   (GB) .................................. 1315762.3

(51) Int. Cl.
*A61B 5/04*    (2006.01)
*A61B 5/11*    (2006.01)
(Continued)

(52) U.S. Cl.
CPC .......... *A61B 5/1128* (2013.01); *A61B 5/0077* (2013.01); *A61B 5/113* (2013.01);
(Continued)

(58) Field of Classification Search
USPC .................................................. 600/476, 532
See application file for complete search history.

(56) References Cited

U.S. PATENT DOCUMENTS

2009/0326388 A1    12/2009  Watson et al.
2012/0123288 A1*    5/2012  Van Kesteren ........ A61B 5/082
                                                       600/532

FOREIGN PATENT DOCUMENTS

EP    1 380 493 A1    10/2011
EP    2 380 493 A1    10/2011
(Continued)

OTHER PUBLICATIONS

Lopez-Meyer et al, "Automatic breathing segmentation from wearable respiration sensors," Fifth International Conference on Sensing Technology (ICST), pub. 2011, IEEE, pp. 156-160.
(Continued)

*Primary Examiner* — Nicole F Johnson
*Assistant Examiner* — Nicole F. Lavert
(74) *Attorney, Agent, or Firm* — Ware, Fressola, Maguire & Barber LLP

(57) ABSTRACT

A method of analyzing breathing data representing a shape of the trunk of a subject 104 as a function of time to monitor and/or analyze the subject's breathing pattern. The data is measured and processed into a data array relating to a 2-dimensional grid having grid points, a position in space of the shape at each grid point and points of time. The method includes the steps of mapping the data array onto a 2-dimensional array, decomposing the 2-dimensional array and forming a signature of the subject 104 from the decomposed 2-dimensional array representing a motion pattern.

20 Claims, 9 Drawing Sheets

(51) Int. Cl.
*A61B 5/113* (2006.01)
*G01B 11/16* (2006.01)
*G06T 7/00* (2017.01)
*A61B 5/00* (2006.01)
*G06T 7/246* (2017.01)

(52) U.S. Cl.
CPC ............ *A61B 5/1135* (2013.01); *A61B 5/725* (2013.01); *A61B 5/7278* (2013.01); *A61B 5/7282* (2013.01); *G01B 11/167* (2013.01); *G06T 7/0016* (2013.01); *G06T 7/246* (2017.01); *G06T 2207/10016* (2013.01); *G06T 2207/30061* (2013.01)

(56) References Cited

FOREIGN PATENT DOCUMENTS

| WO | 00/74631 A2 | 12/2000 |
| WO | 2006/055917 A2 | 5/2006 |
| WO | 2010/021556 A1 | 2/2010 |
| WO | 20101066824 A2 | 6/2010 |
| WO | 20121080896 A1 | 6/2012 |
| WO | 20121090896 A1 | 6/2012 |

OTHER PUBLICATIONS

Moyles et al, "A nonparametric statistical approach to breath segmentation," IEEE Engineering in Medicine & Biology Society 11th Annual Conference, pub. 1989, pp. 330-331.
UK Search Report, Application No. GB1322435.7, dated Nov. 27, 2014, 2 pages.
Int'l Search Report, Int'l Application No. PCT/GB2013/053140, dated May 13, 2014, 6 pages.

* cited by examiner

ANALYSIS OF BREATHING DATA

FIELD

The invention relates to a method of measuring and/or analysing breathing data and to a device for carrying out the method.

BACKGROUND

Monitoring the breathing and/or lung functions of a subject provides data that is often useful for detecting and/or diagnosing the presence of lung disease and/or pulmonary obstructions and/or other conditions. Accurate measurement and analysis of breathing and/or lung functions generally requires the use of devices such as masks or mouthpieces coupled to the mouth of a subject to be monitored. These devices tend to be uncomfortable and/or invasive and do not lend themselves to monitoring difficult and/or frail subjects, for example neonatal subjects.

Respiratory Inductance Plethysmography is another method of monitoring the breathing and/or lung functions of a subject, which is carried out by measuring the movement of the chest and abdominal wall. This approach is based on the theory that the sum of the changes in the anteroposterior diameter of the abdomen and the rib cage correspond to changes in lung volume. Two elastic bands that incorporate sinusoid wire coils are used to measure this diameter. One of the bands is placed around the rib cage under the armpits and the other around the abdomen at the level of the umbilicus.

Expansion of the bands changes the self-inductance of the coils, allowing the change in the anteroposterior diameter to be measured. The bands are connected to an oscillator and demodulation electronics, which convert the readings into digital waveforms. These waveforms are then used to analyse and/or describe various measures of complex respiratory patterns, for example respiratory rate, tidal volume, minute ventilation, peak inspiratory flow, fractional inspiratory time, peak and/or mean inspiratory and/or expiratory flow measures and the percent contribution of the chest and/or abdomen to the tidal volume.

The fitting of the bands on the subject to be monitored requires manoeuvring of the subject, which can in some cases be problematic in difficult and/or frail subjects.

Another known method and associated apparatus for monitoring the breathing and/or lung functions of a subject is disclosed in international publication number WO2010066824 published Jun. 17, 2010 (based on international application number PCT/EP2009/066790 file Dec. 10, 2009 with international phase concluded Jun. 11, 2011) together with an apparatus for carrying out the method, the contents of which are incorporated herein. This method involves an optical measurement of the three-dimensional shape of the body of the subject over time and derives breathing volume data from the changes in shape. Breathing data of the subject may be compared with breathing data associated with healthy and disease states in a statistical database to diagnose the subject's lung function.

It is desirable to provide a method of processing the measurement data that allows a more accurate diagnosis to be made.

SUMMARY

In accordance with a first aspect of the invention, there is provided a method of analysing a data array of at least three dimensions representing a shape of at least part of a body of a subject as a function of time, the data array relating to a 2-dimensional grid having grid points, a position in space of the shape at each grid point and points of time, the method including the steps of:
  mapping the data array onto a 2-dimensional array,
  decomposing the 2-dimensional array,
  forming a signature of the subject from the decomposed 2-dimensional array representing a motion pattern of the shape.

The decomposed 2-dimensional array allows one to derive easily the principal modes of the movement of the body, in particular of the chest or rib cage and/or abdomen or of the left and/or right side or sides of the trunk or chest or rib cage and/or abdomen. The principal modes may relate to chest surface movement patterns. The signature may be derived from the principal modes. In breathing analysis, the signature represents the unique breathing pattern of a subject.

Since a principal mode provides specific information about the motion of a subject, it can distinguish more accurately between disease states than a global parameter such as the volume derived in spirometry. In breathing analysis, the principal modes capture often subtle and localised regional changes of the chest wall, whereas volume, being a global derivative of movement of the chest wall as a whole, does not capture these changes. Therefore, principal modes allow a more accurate diagnosis to be made.

Each row of the 2-dimensional array may correspond to a grid point and/or includes a plurality of positions at the points of time. The decomposition may use singular value decomposition. The decomposed 2-dimensional array may be USVT, U, S and VT being two-dimensional arrays, and/or the signature may be derived from the columns of U that give the largest contribution to the measured motion and/or the signature may include one or more frequencies derived from the first columns.

Another feature of the invention provides a method of populating a database with signatures of different disease states, the signatures being measured using the method described above.

The method may include the step of comparing the signature of the subject with signatures associated with disease states and/or determining a distance between the signature of the subject and the signatures associated with disease states. The signature of a disease state may be derived from the signatures averaged over a group of subjects having the same disease state.

In accordance with a second aspect of the invention, there is provided a method of identifying breaths in parameter values representing a breathing pattern over time, including the steps of:
  forming a time average of the parameter values;
  dividing the parameter in segments, each segment lying between subsequent intersections of the parameter and the average;
  determining an extreme value of the parameter within each segment, the extreme value being a start of an exhalation or an end of an exhalation.

The parameter may be a breathing volume. A segment determined by the method includes either the start or the end of an exhalation. If one segment includes the start of an exhalation, the next segment will include the end of that exhalation, the start and end defining an individual breath. The parameter should provide a reasonably accurate representation of the breathing pattern, but it need not be accurate in terms of actual volume or displacement. The method is robust in the presence of errors in the average and to the method of averaging.

The time average may comprise a moving average, such as an exponential moving average and/or may be formed using a low-pass filter, such as a Gaussian filter. A breath may extend from one of the extremes to the second subsequent extreme.

The method of identifying breaths may be used in the above method of analysing a data array by forming a signature over an integer number of breaths, thereby reducing noise in the signature.

In accordance with a third aspect of the invention, there is provided a method of monitoring and/or analysing the breathing and/or lung functions of a subject, e.g. to produce a data array for use in a method according to the first aspect of the invention and/or to produce parameter values representing a breath pattern over time for use in a method according to the second aspect of the invention, the method comprising the steps of:

projecting a pattern of radiation onto at least part of a body of a subject;

recording at each of a plurality of instances in time image data representing a three dimensional configuration of at least a portion of the projected pattern at that instance in time; and processing the image data to produce a data array, e.g. of at least three dimensions and/or representing a shape of at least part of the body of the subject as a function of time, and/or to produce parameter values representing a breath pattern over time.

The method according to the first and/or second aspect of the invention may further comprise dividing the data array into two or more sub-arrays each representing a three dimensional configuration of a respective part of the projected pattern or of the subject. The method may also comprise processing the sub-arrays to approximate a volume of each of the parts of the projected pattern or of the subject over time. Additionally, the method may include calculating a comparative parameter representing the change over time in the relative volume contribution of each of the parts of the projected pattern or of the subject.

In some embodiments, the comparative parameter comprises a phase angle, which may comprise an overall phase angle calculated from image data across all of the plurality of instances in time or a windowed phase angle calculated from image data across only some of the plurality of instances in time. The comparative parameter may comprise a breath phase angle calculated from image data across the instances in time that correspond to one breath. In some embodiments, the windowed phase angle comprises a predetermined number of breaths. The method may further comprise categorising the breathing or lung function as synchronous or asynchronous or paradoxical.

The comparative parameter may comprise a principal angle and/or spread, which may be calculated using principal component analysis, for example by calculating a covariance matrix, e.g. and diagonalising the covariance matrix.

The method may further comprise calculating one or more of respiratory rate, for example the number of breaths per minute, and/or tidal volume, e.g. the volume inspired and expired with each breath, and/or minute ventilation, e.g. tidal volume multiplied by respiratory rate, and/or peak inspiratory flow, e.g. reflecting respiratory drive, and/or fractional inspiratory time, and/or an index of rapid shallow breathing and/or peak and/or mean inspiratory and/or expiratory flow measures and/or the percent contribution of the chest and/or abdomen to the tidal volume.

The method may further comprise analysing or determining or quantifying the regularity and/or unpredictability and/or randomness of the measured data or one or more of the calculated parameters. The method may comprise calculating a value indicative of disorder (or, in other words, complexity or randomness), preferably an entropy value, e.g. approximate entropy or sample entropy, for one or more values or parameters, for example any of the values or parameters described or listed above, e.g. one or more values of the image data or data arrays or the volume of one or each of the parts or an aggregate volume of the two parts or the comparative parameter.

It has been observed by the applicants that approximate entropy and/or sample entropy, or an equivalent measure of disorder, can provide insight into the state of the subject, for example wherein a predetermined entropy value is indicative of a healthy and/or diseased and/or athletic state of a subject. One specific example of this observation is that entropy of windowed and/or per-breath phase angle appears to decrease in patients with Chronic Obstructive Pulmonary Disease (COPD). For ease of reference, the entropy value or equivalent value may be referred to, for example, as an irregularity value or a coefficient of variation.

In accordance with other aspects of the invention, there is provided an apparatus for carrying out the method, computer software to perform the method and a data carrier storing the software, which software and/or data carrier may be comprised in the apparatus. The apparatus may correspond to the device described in the above-mentioned international publication number WO2010066824 or any other suitable apparatus. The skilled person would also appreciate that some of the steps or aspects of the methods described above may be carried out using data acquired using Respiratory Inductance Plethysmography.

BRIEF DESCRIPTION OF THE DRAWINGS

Certain embodiments of the invention will now be described, by way of example only, with reference to the accompanying drawings, in which.

DETAILED DESCRIPTION OF THE CERTAIN EMBODIMENTS

Figure 1:
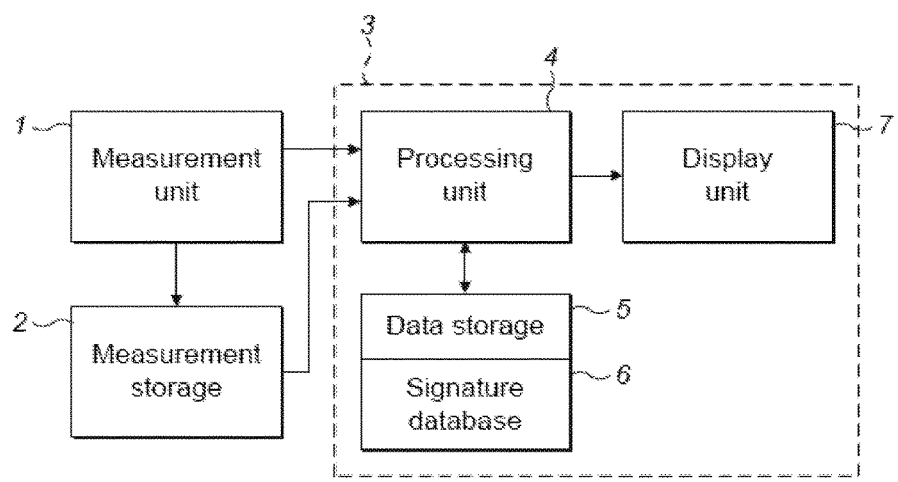
FIG. 1 shows a block diagram of a measuring system.

FIG. 1 shows a block diagram of an embodiment of a measuring system for measuring a 4-dimensional data array of the shape of the body of a subject and analysing the data. The measurement system includes a measurement unit 1 for measuring the shape of a body as a function of time. The system may measure movement of a subject using a method as disclosed in patent application WO 2010066824 or any other method providing similar measurement data. The measurement data of the measurement unit may be stored in a measurement storage 2 for later use or use at a different location.

The measurement system further includes an apparatus 3 for analysing the measurement data. The analysis is carried out by a processing unit 4 of the apparatus; the analysis may be carried out independently from the measurement. The processing unit may receive the measurement data from the measurement storage 2, for example when the measurement unit and the apparatus are at different locations or measurement data is analysed at a time after the measurements were taken. It may also receive the measurement data directly from the measurement unit 1, for example when the measurement unit is located near the apparatus or the measurement unit and apparatus are integrated in a single device. The processing unit can store data in and retrieve data from a data storage 5, such as disc drives or Solid State Drives (SSDs). The data storage may include a signature database 6, which can be used for classifying measured subjects. Results of the analysis can be output to and shown on a display unit 7.

The processing unit 4 and the data storage 5 may form part of a computing device. Its components may be interconnected using a systems bus. Other components may be a volatile memory such as a random access memory; an input/output interface; input devices such as a keyboard; one or more interfaces for communicating with e.g. the measurement unit 1 and the measurement storage 2.

The measurement unit 1 measures movement of a part of the body, in particular of the chest wall and/or the abdomen. Normally, the anterior part of the body is measured; alternatively or in addition a posterior or more or less lateral part may also be measured. When measuring the breathing of a subject, such as a human or an animal, the movement of the chest wall is usually measured. Instead or in addition the movement of the abdomen may be measured. The method produces reliable results both for tidal breathing and for forced manoeuvres; the classification of the subject is consistent between measurements on tidal breathing and forced manoeuvers, where the latter might contain movement artefacts. The present method allows classification of a subject on respiratory diseases using tidal-only breathing data. Prior art methods, using for example flow-volume loops, require the subject to perform a forced breathing manoeuvre. The method is therefore suitable for determining the breathing pattern of healthy and sick subjects, even of unconscious subjects.

The shape of the body is measured using a measuring grid having a 2-dimensional pattern of grid points. Such a grid can be realized by illuminating the body with a chessboard pattern as disclosed in the above mentioned patent application WO 2010066824. The 3-dimensional position of the body is measured at each grid point as a function of time. The grid has $n_1$ by $n_2$ grid points; $n_1 \times n_2$ may be 10×15, resulting in $n_g=150$ grid points. When images of the body are captured with a video camera operating at 30 frames per second with a measurement time of 4 seconds, the position of the body for each grid point will be measured at $n_t=30*4=120$ points in time. The present analysis method, providing a decomposition of the body surface movement into modes, requires only a relatively short period of measurements, usually only a few seconds in duration, without the need for the subject to perform a forced manoeuvre. An analysis of breathing modes can be made on just a small section, e.g. 6-10 seconds, of tidal breathing. As a consequence, the method can be applied even to subjects that are not capable of forced manoeuvres and allows a quicker measurement of patients.

The data of a measurement of a subject output by the measurement unit 1 includes $n_t$ frames of $n_1*n_2$ 3-dimensional positions. If a position is represented by three spatial dimensions (x,y,z), the data output is $n_t*n_1*n_2*3$ numbers. The data can be organized in a 4-dimensional array A, two dimensions being for the grid, one dimension for the position and one dimension for the time. Alternatively, the data can be organized in a 3-dimensional array, one dimension being for the grid, one dimension for the position and one dimension for the time. The grid can be represented by a 1-dimensional array having elements 1 to $n_g$, where each element relates to one grid point of the grid. The data may be input to the measurement storage 2 or to the processing unit 4.

It should be noted that the word 'dimension' is used in two different contexts. When used in the context of an array, it refers to the array dimension. When used in the context of position, it refers to the spatial dimension.

Figure 2:
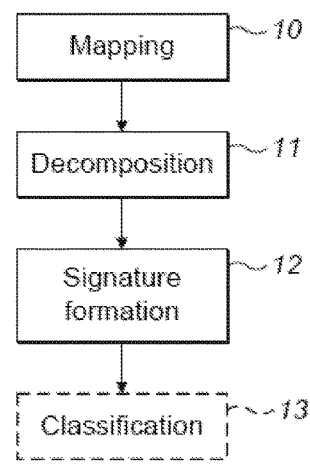
FIG. 2 shows a flow diagram of the method.

The processing unit 4 analyses the data array A by carrying out the three steps of mapping, decomposition and signature formation, shown as steps 10, 11 and 12, respectively in the flow diagram of FIG. 2.

The first step is mapping the data array A onto a 2-dimensional array M(i,j). The mapping may be carried out such that each row of M corresponds to a grid point. When the different rows of the 2-dimensional array correspond to different grid points, the principal modes that can be derived from the decomposition of M correspond to properties of the chest wall movement as a function of the grid point. Such spatially separated information is useful in diagnosis. If the grid includes $n_g=n_1*n_2$ grid points, the 2-dimensional array will have $n_g$ rows relating to the grid points. The index i of the array M(i,j) relates to the grid points and numbers from 1 to $n_g$.

The data array may be mapped onto M such that each row includes a plurality of positions at the points of time where the measurements were taken. In this embodiment, the data array includes positions for each grid point at $n_t$ moments in time and each position represents a point (x,y,z) in 3-dimensional space. These $n_t$ positions are mapped onto the rows of the 2-dimensional array M such that M will have $3n_t$ columns. The index j of M(i,j) runs from 1 to $3n_t$. If $n_1=10$, $n_2=15$ and $n_t=120$, the matrix M is 150×360. When the rows correspond to the grid points and the columns to the position of these grid points on the body as a function of time, the principal modes will be surface modes of the measured subject, representing breathing patterns. Many lung diseases have characteristic surface modes, making the modes particularly useful in diagnosis.

The data array may be mapped onto M in other ways. For example, it may be mapped onto an array M of $n_t \times (3*n_1*n_2)$. Each of the $n_t$ rows corresponds to a particular point of time and gives the $n_1*n_2$ positions of the grid at that moment in time. The resulting modes will represent time signatures.

The second step in the analysis is the decomposition of the array M into principal modes by the processing unit 4, shown as step 11 in FIG. 2. Several methods for decomposition may be used, of which Singular Value Decomposition (SVD) is a fast method that works efficiently on very large matrices; see e.g. 'A multilinear singular value decomposition' by Lathauwer et al. in Siam J. Matrix Anal. Appl., Vol. 21, No 4, pp. 1253-1278. Matrix M of $n_g$ rows by $3n_t$ columns is decomposed so that $M=USV^T$. U is a unitary matrix of $n_g \times n_g$, S is a diagonal matrix of $n_g \times 3n_t$, and $V^T$ a unitary matrix of $3n_t \times 3n_t$. $V^T$ is the conjugate transpose of V. The columns of U are the eigenvectors of $MM^T$; they are orthogonal and normalised. The diagonal values of S are the square roots of the non-negative eigenvalues of both $M^T M$ as well as $MM^T$. The columns of V are eigenvectors of $M^T M$. The elements of U and S are independent of time. The time dependence of the measured motion is included in the matrix $V^T$.

The third step of the analysis carried out by the processing unit 4 is the formation of a signature of the subject, shown as step 12 in FIG. 2. The signature may be stored in the data storage 5 of the apparatus 3. The columns of the matrix U represent the principal modes of the breathing pattern of the measured body. When the motion of the chest wall of a subject is measured, the principal modes are the breathing patterns of the subject. The measured motion is best characterized by low-numbered columns of U, i.e. by the modes that give the largest contribution to the measured variation of the surface during breathing.

The first columns of U may represent a static orientation of the body, which may not be relevant for classification of a subject. For example, the first two or three columns represent the main planar orientation of the subject. The columns representing static orientation may be omitted from the signature. The number of columns of U selected for the signature can be determined by choosing those columns of U that correspond to diagonal elements of S which are above a predetermined value, possibly excluding columns relating to static orientation. In the analysis of breathing patterns 2, 3, 4, 5 or 6 modes are normally sufficient for classification. Higher order modes can usually be ignored, because they provide a very small contribution to the breathing pattern and may represent only noise.

In addition to using columns of U for the signature, parts of the matrix S and/or V may be used. For example, the weight in the matrix S may be included in the signature, which could be done by weighting the columns of U with the corresponding eigenvalues of S. The method of combining the information in U, S and/or V may be dependent on the type of classification used.

Since U is time independent, it is useful for forming the signature. Moreover, measurement data taken at different times or taken from different subjects do not have to be normalised to a specific, predetermined breathing rate before deriving the eigen modes, as is necessary in some prior art analysis methods. The important surface movement patterns of the chest are contained in the first few principal modes of U. Therefore, more information is obtained about the subject than from a volume measurement using a prior art method, as the latter does not distinguish between modes. In determining the volume, all localised surface movement information is discarded. It is this information that is used in a classification. The modes are the most important parts of the breathing pattern and are therefore included in the signature.

Figure 3:
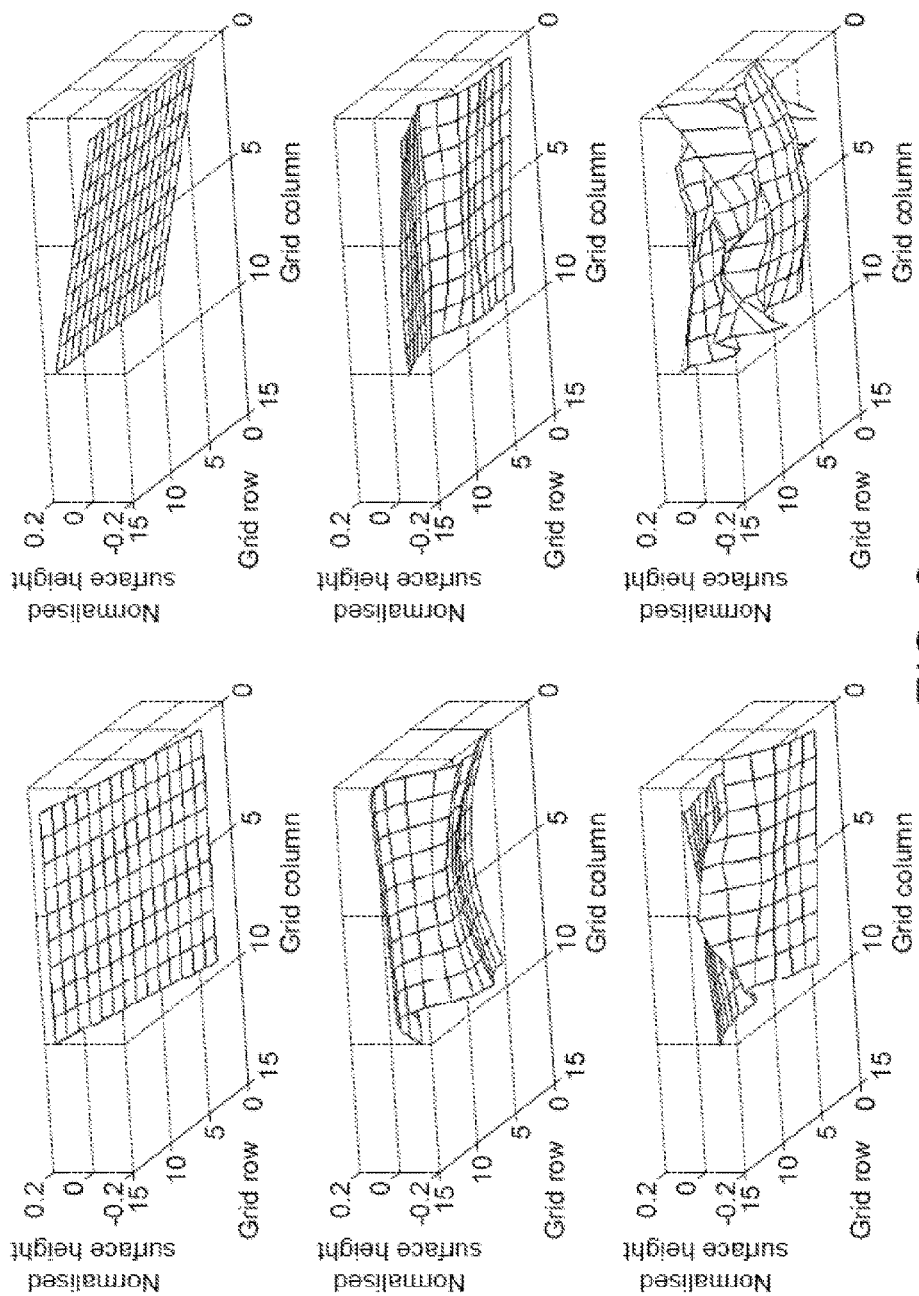
FIG. 3 shows six breathing modes of a healthy subject.
Figure 4:
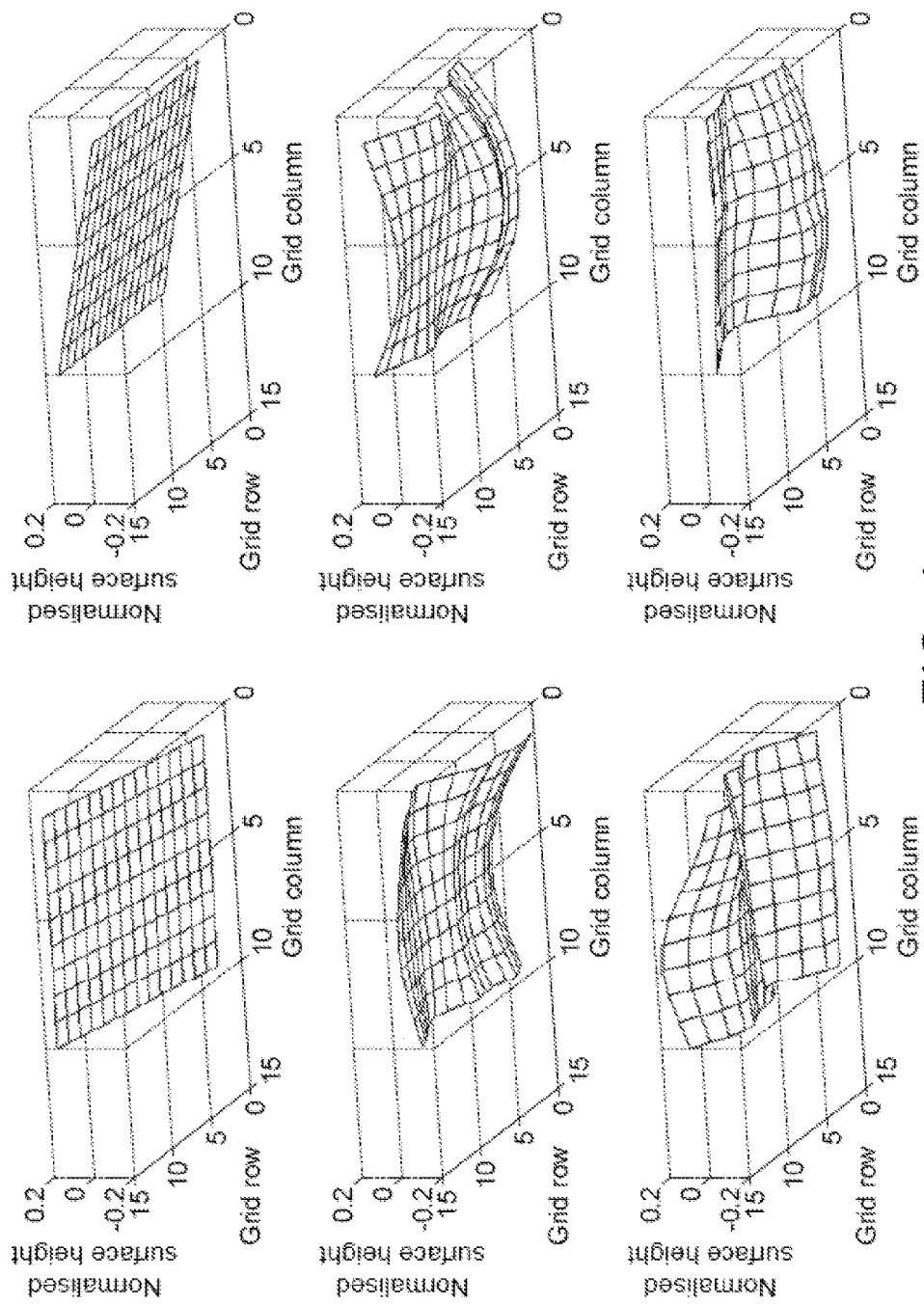
FIG. 4 shows six breathing modes of a subject suffering from COPD.

FIG. 3 shows a graphical presentation of the first six breathing modes of a healthy subject during tidal breathing and the first part of a forced expiration. The order of the modes in the Figure is from left to right and top to bottom. Grid rows go from abdomen to chest with ascending row number. Grid columns go from the left side of the chest wall to the right side, with ascending column number. The presentation can be displayed on the display unit 7. The visualisation is obtained by taking a column of U and unwrapping it by distributing its $n_g$ elements over an $n_1 \times n_2$ array. The result is shown in the Figure as a surface on an $n_1 \times n_2$ grid. The example shown in FIG. 3 has a grid of 15×10 grid points. The vertical axis shows the dimensionless, normalised position of the mode. FIG. 4 shows the first six breathing modes from the matrix U of a Chronic Obstructive Pulmonary Disease (COPD) patient during tidal breathing and the first part of a forced expiration. The first two modes of both FIGS. 3 and 4 represent static orientation of the body.

The importance of each breathing mode is represented by the corresponding eigenvalue of the matrix S. The six eigenvalues corresponding to the six modes of the healthy subject in FIG. 3 are: 134.78; 93.36; 16.57; 5.30; 0.73; 0.29. The small eigenvalues for the last two modes indicate that these modes are less important because they contribute only a very small amount to the measured chest motion; these modes may be at least partly noise. The six eigenvalues for the six modes of the COPD patient in FIG. 4 are: 160.19; 109.11; 18.56; 4.71; 1.42; 0.57.

Figure 5:
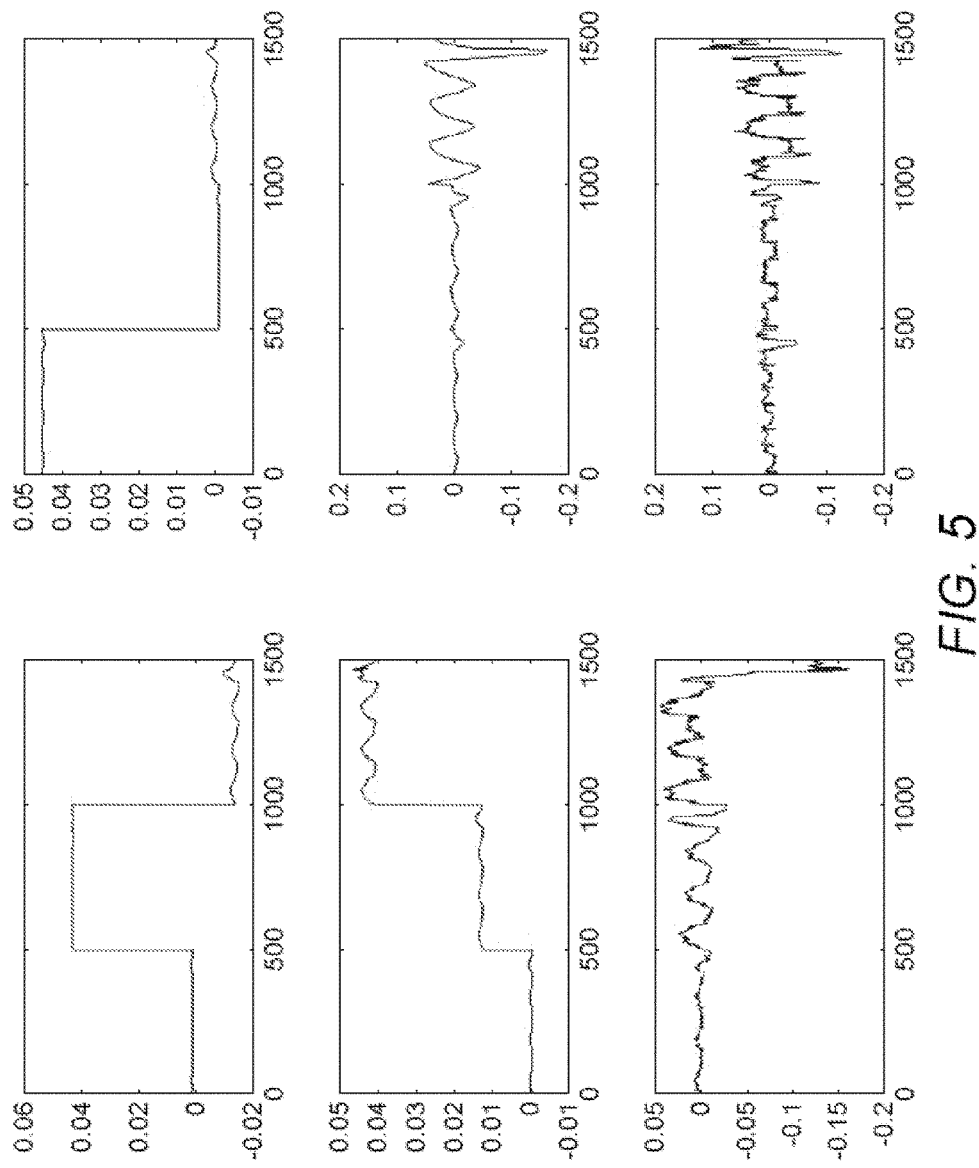
FIG. 5 shows the time evolution of the modes of FIG. 3.
Figure 6:
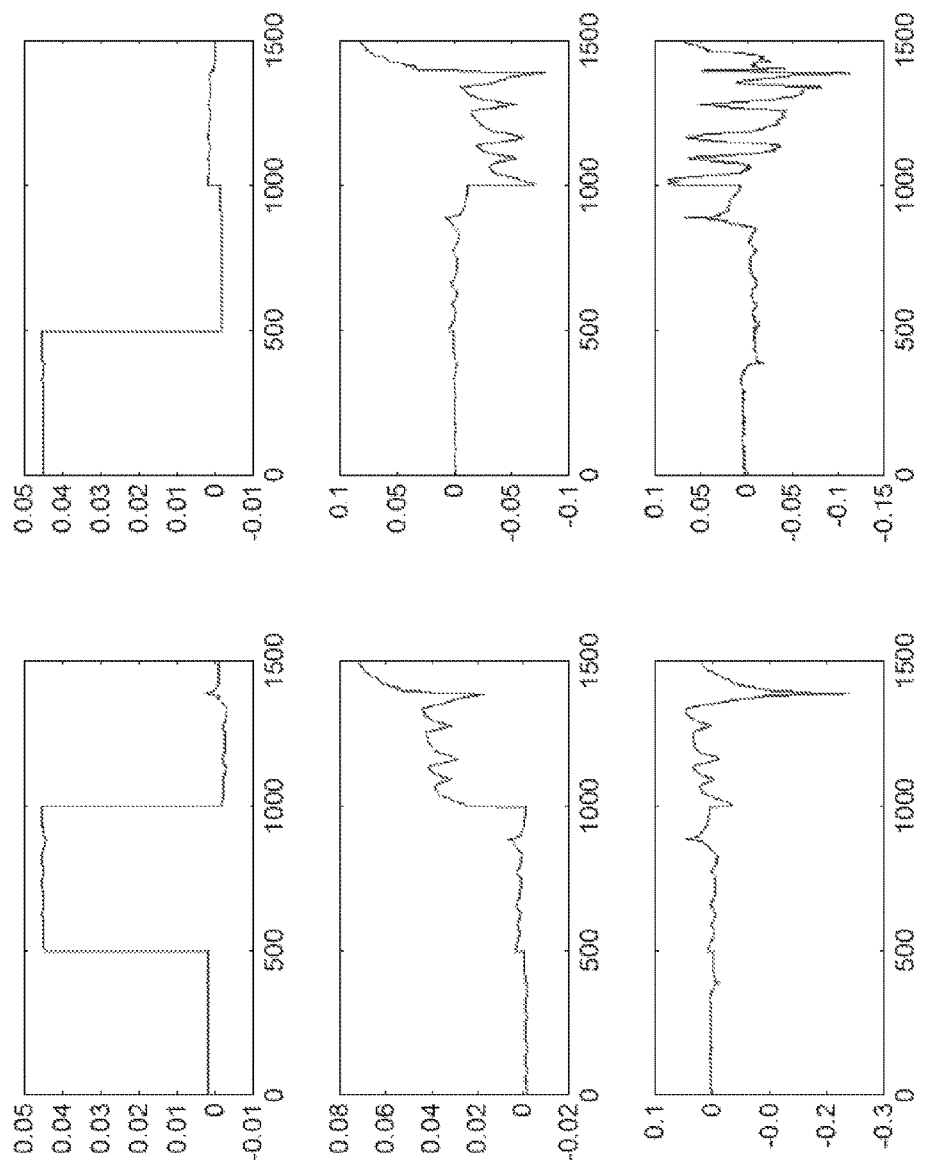
FIG. 6 shows the time evolution of the modes of FIG. 4.

The columns of V give a normalised time series of how the modes move in the x, y and z direction. FIGS. 5 and 6 show plots of the first six columns of V corresponding to the six breathing modes shown in FIGS. 3 and 4, respectively. The horizontal axis of each of the six plots represents the frame number from 1 to 1500, subdivided into three parts for the coordinates x, y and z. The vertical axis of the plots represents the number by which the coordinate must be multiplied to obtain the time evolution of the mode. The first 500 frames represent the value with which the x coordinates of all grid points of a corresponding mode must be multiplied. The next 500 frames represent the values for the y coordinate and the last 500 frames for the z coordinate.

The time evolution of each of the modes or a combination of modes can be visualised on the display unit 7 by combining the one or more mode shapes of U, the one or more corresponding magnitudes of S and the one or more corresponding time dependences of V. The combination can be made by calculating $M=USV^T$ for the relevant modes.

Instead of or in addition to using the modes of U in the signature, features extracted from U may be used in the signature. One such feature is the 2-dimensional frequencies of each mode, which may be formed via a 2D Fourier transformation of a mode. The 2-dimensional frequencies of certain modes are characteristic for specific disease states, such as disorders of the lungs, and are therefore suitable for classification.

The features extracted from the decomposed matrix A and combined in a signature of a measured subject may be used to classify the subject. The classification is shown as a step 13 in FIG. 2, which can be included or can be omitted from the method. In the classification step the signature of the subject is compared to previously generated signatures stored in the database 6. Each of these previously acquired signatures is representative of a particular disease state, including, but not limited to, COPD, asthma, pneumonia, or a healthy state. The result of the classification is an association of the breathing signature of the subject with a particular disease state or the healthy state or the closeness to such a state.

The database 6 stores the signatures of a large number of subjects, each labelled with its disease or healthy state. The disease state may include the disease progression. The measurement data arrays of the subjects are analysed, usually offline, and the signatures formed.

A clustering algorithm forms clusters of signatures for each of the disease labels and stores them in the database. A simple form of classification consists of reducing each of the cluster members to an average value and an approximate radius, for example a standard deviation. The result is a representative signature for each disease class and an expected spread of the members of this class from the representative signature. In another form of classification the labelled cluster members or their extracted feature vectors are kept in the database for use in a subsequent classification via a k-nearest neighbours method. The database can be updated and refined when additional labelled signatures become available. The larger the number of labelled signatures, the more accurate is the classification. Good results are obtained when each cluster has at least 40 signatures. The classification is improved if the signatures in the database have been obtained under similar conditions, such as lighting environment, breathing manoeuver, grid coverage, grid size and patient position. On the other hand, the population of signatures should capture as wide a range of conditions in which the system is to be expected to perform.

The actual classification of a subject is carried out in the processing unit 4. The distance of the signature to the representative signature of each cluster is determined, known as classification or k-mean search. Alternatively, the label of the signature can be assigned as the most common label among its k nearest neighbours, where 'nearest' implies 'smallest distance'. The output of the classification step can be that the subject is in the disease state corresponding to that of the representative signature his signature is nearest to, or, for each disease label, a probability that subject is in that particular disease state.

The method as shown in FIG. 2 includes mapping, decomposition and signature formation, together forming the analysis of the data array. The results of the analysis may be stored and used later for classification by a physician or for other purposes. The analysis may also be followed by a classification using a signature database, forming a four-step method shown by elements 10-13. In a special embodiment the analysis is preceded directly by a step in which a subject is measured and the data array is filled; the analysis may again be followed by a classification.

Rows and column of a matrix can be interchanged in the composition of the matrices U, S and V. Although the above described embodiments refer to a rectangular coordinate system (x,y,z), any other coordinate system may be used, e.g. a cylindrical coordinate system having its axis along the longitudinal axis of the body.

The signature formed from the measured data becomes more accurate if the data on which the signature is based relates to a whole number of breaths. It could be regarded as 'normalising' the data input to the signature decomposition. This can be achieved by analysing the data and manually selecting the desired integer number of breaths. The following method allows to automate the selection of breaths, making the analysis less time consuming.

Figure 7:
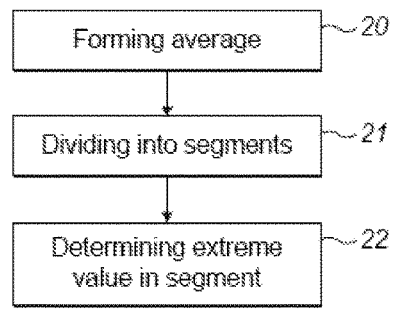
FIG. 7 shows a flow diagram of the breath detection method.

FIG. 7 shows a flow diagram of a breath detection method for identifying individual breaths or a series of breaths. Measured parameter values representing a breathing pattern over time are input to the method. The parameter can e.g. be a measured breathing volume or a chest wall motion over time. The breathing volume may be obtained from a spirometer. If the method of FIG. 7 is used together with the method of FIG. 2, the breathing volume or chest wall movement over time may be derived from the above matrix M or from $USV^T$. In the latter case, noise in the method can be reduced by using only the most significant modes of U in the calculation of the motion. The parameter can also be an average of the z-position over the measurement grid.

Figure 8:
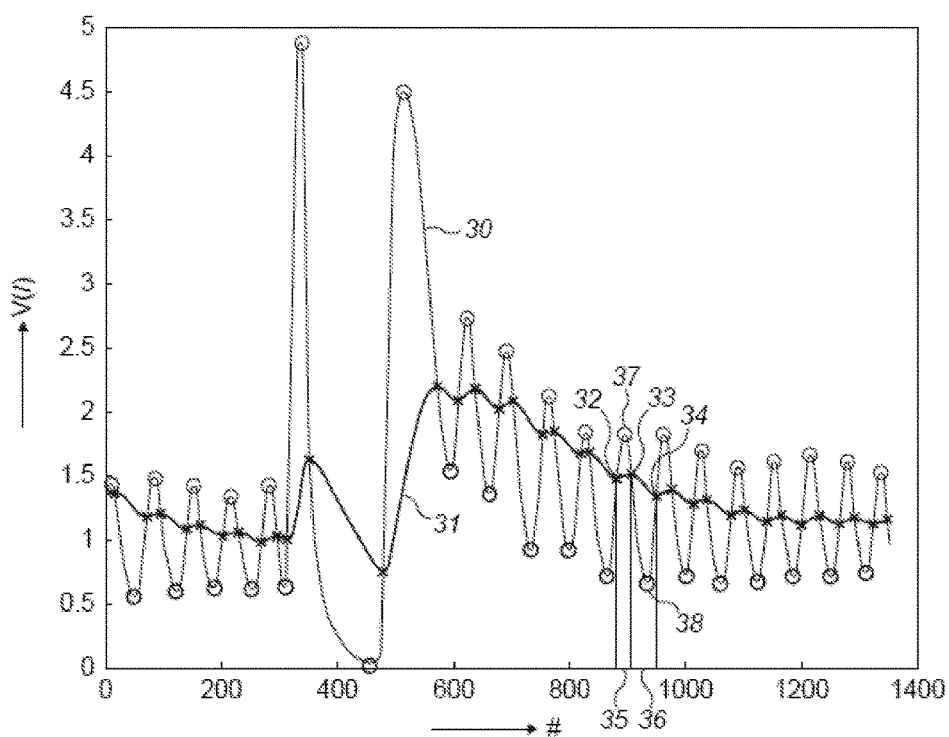
FIG. 8 shows a measurement of breathing volume.

FIG. 8 shows a measurement 30 of breathing volume V over time t of a subject; the measurement includes tidal breathing and one forced manoeuvre. The vertical axis shows the volume in liters, the horizontal axis shows time in frame numbers, taken at 30 frames per second. A measurement of chest wall motion would have resulted in a similar plot. The measured parameter values are used as input for the method of FIG. 7.

In the first step 20 in the method of FIG. 7 an average value of the parameter values is formed. The average may be an exponential moving average. When the parameter values V are given at discrete points of time i, the average A can be determined as $A(i)=(1-\alpha)A(i-1)+\alpha V(i)$. Alpha can have any value in the range [0,1]. Good results for a wide range of input are obtained using a value of alpha equal to 0.008. The moving average is shown in FIG. 8 as line 31.

The average may be determined by other algorithms, e.g. using a low-pass filter having a Gaussian response function. In a specific embodiment the filter can have a size of three times the sample rate and a sigma equal to the sample rate, where the sample rate is the number of frames per second of the measurement unit.

In the second step 21 of the method the parameter is divided in time segments. Each segment lies between subsequent intersections of the parameter and the average. FIG. 8 shows three consecutive intersections 32-34, defining two successive segments 35 and 36. The method is not sensitive to the way in which the intersections are determined. An intersection may be defined as the point in time where $(V(i)-A(i))$ changes sign.

In the third step 22 of the method an extreme value of the parameter within each segment is determined. An extreme value may be determined by comparing a value of the parameter with its two neighbouring values. The method will find the maximum 37 as extreme values for segment 35 and the minimum 38 for segment 36 as shown in FIG. 8. If the extreme value of a segment is a maximum, it corresponds to the end of an inhalation and the start of an exhalation. If the extreme value is a minimum, it corresponds to the end of an exhalation and the start of an inhalation. The method can be made more robust by checking whether the extreme value V(i) is larger than the average A(i) for a maximum and whether the extreme value is smaller than the average for a minimum. Alternatively, the signed area of $(V(i) A(i))$ over the segment can be determined; an extreme value in a segment having a positive area is a maximum, corresponding to the start of an exhalation and an extreme value in a segment having a negative area is a minimum, corresponding to the start of an inhalation.

Since each segment has only one extreme value of the parameter, it must include either the start of an exhalation (being the end of an inhalation) or the end of an exhalation (being the start of an inhalation). Hence, if a segment includes the start of an exhalation, the next segment will include the end of the exhalation. An individual breath, including an inhalation and an exhalation, corresponds to the period between two successive maximum values or between two successive minimum values. A selection of measurement data extending over a certain number p of whole breaths can be made by starting the selection at the point of time of an extreme value of the parameter and stopping the selection at the $2p^{th}$ extreme value of the parameter following the starting point.

The method can be carried out in an apparatus similar to apparatus 3 in FIG. 1 including a processing unit 4 and a data storage 5, forming a computer device. In a real-time implementation the apparatus is connected to the output of a measurement unit and measured values are fed into the apparatus. The data may be input in frames at regular intervals, e.g. 30 frames per second. The measured values are pre-processed if necessary to obtain the parameter values required for the method, e.g. a breathing volume or a chest wall motion. In an embodiment in which the above moving average method is used, the moving average is updated at each frame being input into the apparatus, the check for start of a new segment is carried out, and the moving extreme value is updated.

The method of FIG. 7 can be used to determine the start of a signature decomposition by monitoring the breathing of a subject under test, The breath detection method performs an on-line scan of the breaths until it has detected a sufficient number of good quality contiguous breaths, upon which the apparatus 4 is signalled to commence signature decomposition without additional operator intervention.

In on off-line implementation of the method the apparatus is connected to a measurement storage, from which the measured values are retrieved. The processing can be carried out similar to the on-line implementation.

The method of identifying breaths can be used for ventilator settings in respiratory treatment, e.g. for determining volume drift over time in patients with an obstructive disease. It can also be used in the context of ventilator triggering, where the detection of an inhalation (i.e. the end of an exhalation) triggers the administration of oxygen.

The method can also be used for analysing the shape of individual breaths, as is common in the veterinary field. The method is used to segment the measurements in whole breaths.

The method is suitable as a step in forming a signature in the method of FIG. 2. The method may be applied to the data array output by the measurement unit 1 in FIG. 1, e.g. by using the average z-position over the measurement grid as parameter. The steps of mapping, decomposition and signature formation can then be applied to a part of the data array corresponding to an integer number of breaths.

Each of the methods of FIGS. 2 and 7 can be carried out by a computing device in which software is stored in a memory and is coded to execute the method when running in the processing unit. The software may be stored on a data carrier.

Figure 9:
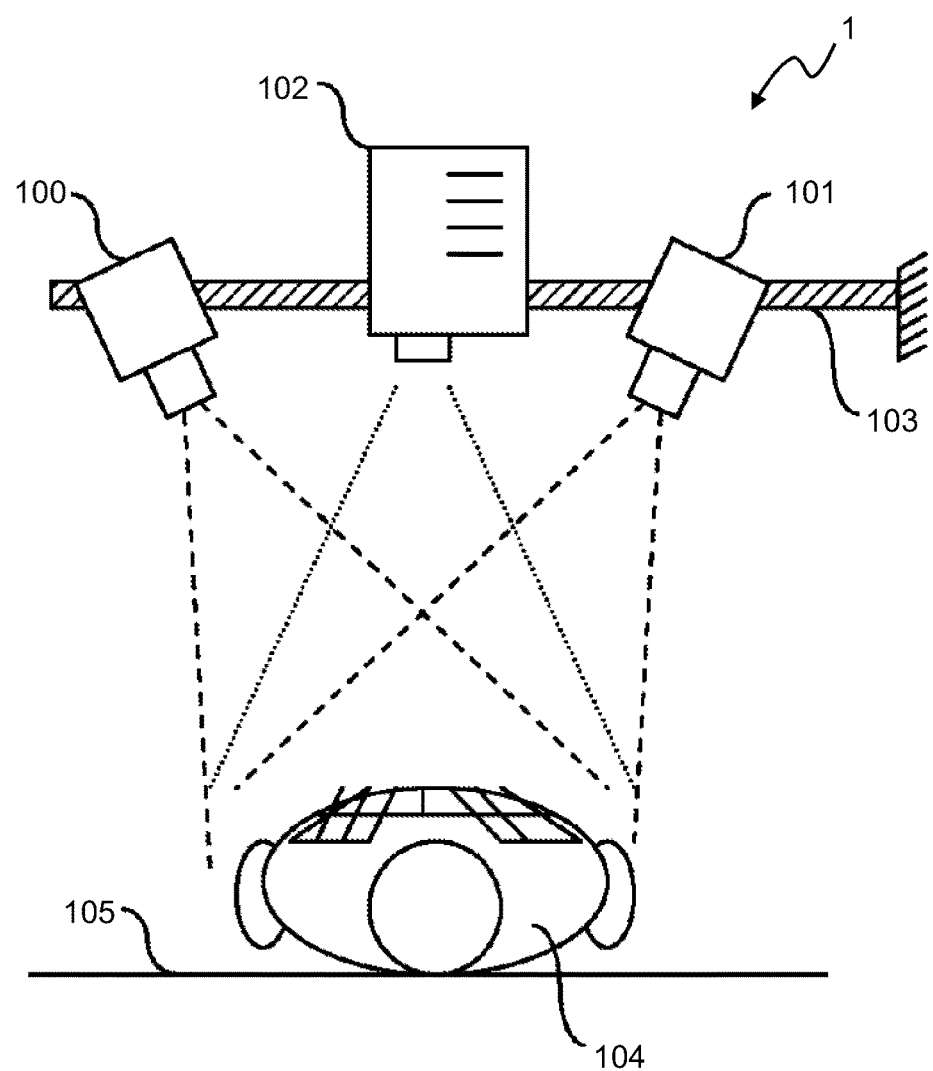
FIG. 9 shows an exemplary embodiment of the measurement unit of FIG. 1.

Referring now to FIG. 9, there is shown an exemplary embodiment of the measurement unit 1 of FIG. 1. The measurement unit 1 includes first and second cameras 100, 101 and a projector 102 attached to a mounting frame 103. The projector 102 projects a pattern of radiation onto the chest and abdominal area of a subject 104 laying prone on a surface 105. The cameras 100, 101 are mounted either side of the projector and are angled toward the subject 104 at an angle of between about 10 degrees to about 40 degrees, depending on the spacing between the frame 103 and the subject 104.

In use, the measurement unit 1 acquires across a predetermined time period from the cameras 100, 101 at each of a plurality of instances in time image data representing a three dimensional configuration of the projected pattern at that instance in time. The image data is then processed to produce an array of breathing data representative of the shape of the subject 104 as a function of time. This data may then be used in accordance with the methods described above.

The data array may also be divided into two or more sub-arrays each representing a three dimensional configuration of a respective part of the subject 104, for example the subject's chest and abdomen or the left and right sides of the subject's trunk region. The sub-arrays may be processed to approximate a volume of each of the parts of the subject over time and may be displayed through the display unit 7, for example to assist a clinician with diagnosing a condition in the subject 104.

The sub-arrays or volumes may also be processed to calculate one or more comparative parameters representing the change over time in the relative volume contribution of each of the parts of the subject 104.

Figure 10:
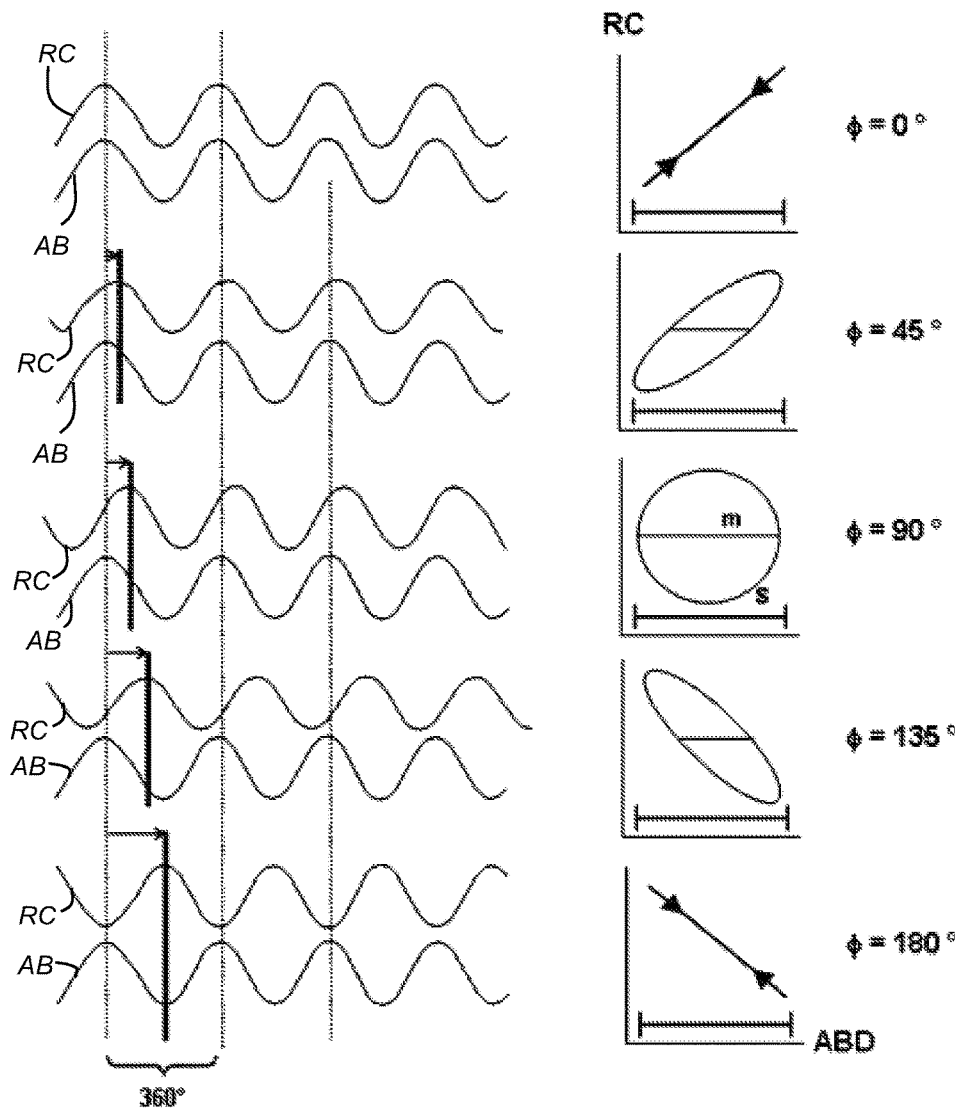
FIG. 10 shows five measures of synchronicity between chest and abdomen volumetric contributions to tidal breathing volume.

FIG. 10 illustrates one such comparative parameter, namely the phase angle $\phi$ between chest or rib cage measurements RC and abdomen measurements AB, where:

$$\phi = \frac{180}{\pi} \times \operatorname{asin}\left(\frac{m}{s}\right)$$

It will be appreciated by those skilled in the art that the phase angle $\phi$ may be calculated across the entire time period (i.e. an overall phase) or across a subset of the entire time period (i.e. a windowed phase). The subset may correspond to a single breath (i.e. a per-breath phase) or a predetermined number of breaths.

Figure 11:
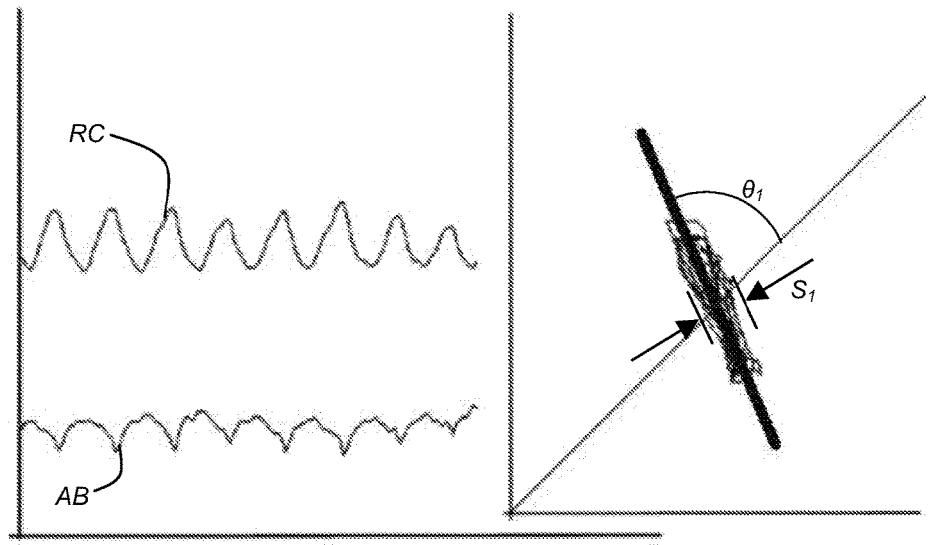
FIG. 11 shows a first example of principal angle and spread between chest and abdomen volumetric contributions to tidal breathing volume.
Figure 12:
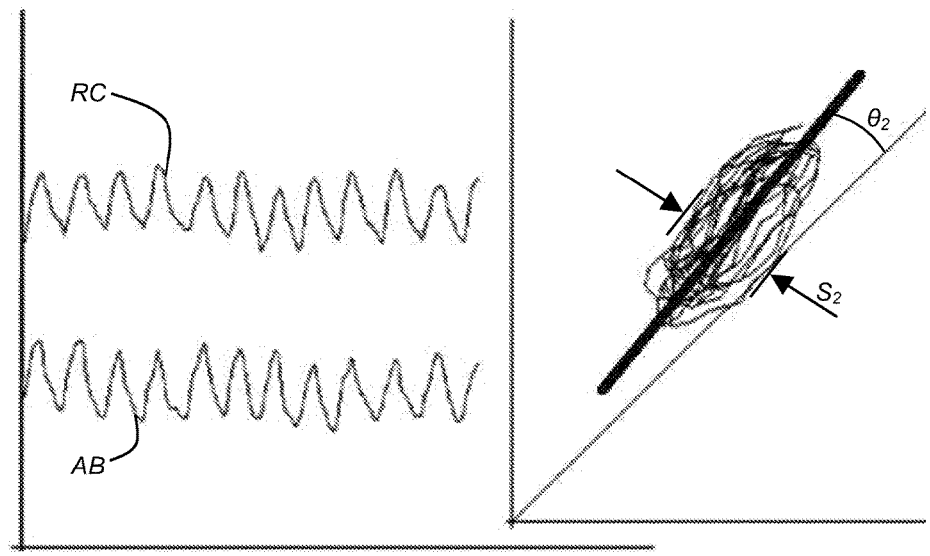
FIG. 12 shows a second example of principal angle and spread between chest and abdomen volumetric contributions to tidal breathing volume.

FIGS. 11 and 12 illustrate examples of two further comparative parameters, namely the principal angle $\theta_1$, $\theta_2$ and spread $S_1$, $S_2$ between chest or rib cage measurements RC and abdomen measurements AB.

These parameters are calculated using principal component analysis by calculating a 2×2 covariance matrix, where $M = \operatorname{Cov}(AB - \operatorname{mean}(AB), RC - \operatorname{mean}(RC))$ and diagonalising the covariance matrix, where:

$$M = [p_1, p_2] \begin{bmatrix} \sigma_1^2 & 0 \\ 0 & \sigma_2^2 \end{bmatrix} [p_1, p_2]^T.$$

The principal angle $\theta_1$, $\theta_2$ is the angle (in degrees) between the x=y line and $p_1$, while the spread is the ratio:

$$\operatorname{spread} = \begin{cases} \frac{\sigma_2}{\sigma_1}, & p_{1,x} p_{1,y} \geq 0 \\ \frac{\sigma_2}{\sigma_1}, & p_{1,x} p_{1,y} < 0 \end{cases}$$

The angle change is also useful to track, which is done by taking three successive points $p_0$, $p_1$, $p_2$, treating these two-dimensional vectors as three-dimensional by making the z-coordinate 0 and performing the three-dimensional cross product:

$$a = (p_2 - p_1) \times (p_1 - p_0)$$

and making the product of its sign and magnitude the angle change.

Further parameters that may be useful to calculate and display on the display unit 7 include respiratory rate, tidal volume, minute ventilation, peak inspiratory flow, fractional inspiratory time, peak and/or mean inspiratory and/or expiratory flow measures and/or the percent contribution of the chest and/or abdomen to the tidal volume.

One particularly useful analysis to carry out is to determine or quantify the entropy of one or more of the measured values or parameters described above. Specifically, the approximate entropy or sample entropy, or an equivalent measure of disorder, of some of the aforementioned parameters have been found to be useful in determining a comparative state of wellness or illness.

In particular, it has been found that the entropy associated with breathing data derived from a healthy subject is higher, in many cases considerably higher, than breathing data derived from an ill patient.

Entropy in the form of sample entropy (SampEn), approximate entropy (ApEn) or fuzzy entropy (FuzzyEn) can be calculated as described, for example, in section 2 of CHEN, W et al. Measuring complexity using FuzzyEn, ApEn, and SampEn, *Medical Engineering & Physics*, 31(1), 61-68, 2009.

The above embodiments are to be understood as illustrative examples. Further embodiments are envisaged. It is to be understood that any feature described in relation to any one embodiment may be used alone, or in combination with other features described, and may also be used in combination with one or more features of any other of the embodiments, or any combination of any other of the embodiments. Furthermore, equivalents and modifications not described above may also be employed without departing from the scope of the accompanying claims.

The invention claimed is:

1. A method, comprising:
performing an external optical measurement of a three-dimensional shape of a body of a subject over time, thereby obtaining measurement data;
processing the measurement data to produce a data array of at least three dimensions representing a shape of at least part of the body of the subject as a function of time, the data array relating to a two-dimensional grid having grid points, a position in space of the shape at each grid point and points of time,
mapping the data array onto a two-dimensional array,
decomposing the two-dimensional array, and
forming a signature of the subject from the decomposed two-dimensional array representing a motion pattern of the shape.

2. The method according to claim 1, wherein the two-dimensional array comprises rows and each row of the two-dimensional array corresponds to a grid point.

3. The method according to claim 1, wherein the two-dimensional array comprises rows and each row of the two dimensional array includes a plurality of positions at the points of time.

4. The method according to claim 1, wherein the decomposing comprises singular value decomposing.

5. The method of claim 1, further comprising:
projecting a pattern of radiation onto said at least part of the body of the subject;
recording at each of a plurality of instances in time image data representing a three dimensional configuration of at least a portion of the projected pattern at that instance in time; and
processing the image data to produce the data array.

6. The method according to claim 1, wherein the decomposed two-dimensional array is $USV^T$, U, S an $V^T$ being two-dimensional arrays, and the signature is derived from the columns of U that give the largest contribution to the measured motion.

7. The method according to claim 5, further comprising: populating a database with signatures of different disease states, the signatures being measured using the method.

8. The method according to claim 7, further comprising comparing the signature of the subject with signatures associated with disease states.

9. The method according to claim 8, further comprising determining a distance between the signature of the subject and the signatures associated with disease states.

10. The method according to claim 8, wherein the signature associated with a disease state is derived from signatures formed using the method averaged over a group of subjects having the same disease state.

11. The method according to claim 7, wherein the signatures associated with disease states are obtained from a database populated with signatures formed using the method.

12. A measurement system comprising:
a measurement unit for measuring a shape of at least part of a body of a subject as a function of time; and
a processing unit for analysing measurement data of the measurement unit, wherein the measurement system is configured to perform the method according to claim 1.

13. A measurement system according to claim 12, wherein the measurement unit comprises first and second cameras and a projector attached to a mounting frame, wherein the projector is configured to project the pattern of radiation and the first and second cameras are configured to obtain the image data.

14. A method of determining a signature characteristic of a motion pattern of a shape of a body part of a subject during breathing, the method comprising:
generating a spatial two-dimensional pattern of observational points on the body part of the subject;
at each observational point, measuring a position of the body part in a third spatial dimension as a function of time during breathing;
mapping the spatial and time data into a data array of at least two array-dimensions;
decomposing the data array into modes of movement of the body part; and
determining a signature characteristic of the breathing pattern of the subject from the decomposition data.

15. The method of claim 14, wherein the body part is the chest and/or abdomen of the subject, or parts thereof.

16. The method of claim 14, wherein the observational points are generated by projecting a pattern of radiation on the body part of the subject.

17. The method of claim 16, wherein the pattern of radiation is a grid having grid points.

18. The method of claim 14, wherein at least one array-dimension corresponds to the observational points, and at least another array-dimension corresponds to the positions of the body part in the third spatial dimension as a function of time.

19. The method of claim 17, wherein at least one array-dimension corresponds to the grid points, and at least another array-dimension corresponds to the positions of the body part in the third spatial dimension as a function of time.

20. The method of claim 14, wherein the data array is decomposed into principle modes of the movement of the body part.

* * * * *